United States Patent [19]
Harrington et al.

[11] Patent Number: 5,808,088
[45] Date of Patent: Sep. 15, 1998

[54] PREPARATION OF MIBEFRADIL VIA AN ACETAMIDE ANION

[75] Inventors: Peter J. Harrington, Louisville; Michael P. Fleming, Longmont, both of Colo.

[73] Assignee: Roche Colorado Corporation, Boulder, Colo.

[21] Appl. No.: 60,151

[22] Filed: Apr. 14, 1998

[51] Int. Cl.$^6$ ................................. C07D 235/14
[52] U.S. Cl. ......................................... 548/309.7
[58] Field of Search ........................... 548/309.7

[56] References Cited

U.S. PATENT DOCUMENTS

| | | | |
|---|---|---|---|
| 4,680,310 | 7/1987 | Hengartner et al. | 514/539 |
| 4,808,605 | 2/1989 | Branca et al. | 514/394 |
| 5,120,759 | 6/1992 | Hengartner et al. | 514/452 |

OTHER PUBLICATIONS

B.M. Trost et al., "New Synthetic Reactions. Alkylation of Lactam Derivatives", *J. Org. Chem.,* 39(16), 2475–6 (1974).

R.P. Woodbury et al., "Isolation and Reactions of α–Lithio N,N–Dimethylacetamide", *J. Org. Chem.,* 42(10), 1688–90 (1977).

V. Bažant et al., "Properties of Sodium–bis–(2–methoxyethoxy)aluminiumhydride. I. Reduction of Some Organic Functional Groups", *Tetrahedron Letters,* 1968, 3303–6.

H.R. Wiltshire et al., "Metabolism of calcium antagonist Ro 40–5967 . . . ", *Xenobiotica* 22(7), 837–57 (1992).

S. Chandrasekaran et al., "Synthesis of Substituted β–Lactams by Addition of Nitromethane . . . ", *J. Org. Chem.,* 42(24), 3972–4 (1977).

D.B. Bryan et al., "Nuclear Analogues of β–Lactam Antibiotics. 2 . . . ", *J. Am. Chem. Soc.,* 99(7), 2353–5 (1977).

G.J. O'Malley et al., "Tremorgenic Mycotoxins: Synthesis of 6–Demethyloxyfumitremorgin C", *Tetrahedron Letters,* 28(11), 1131–4 (1987).

M. Leplawy et al., "Peptides—XI. Synthesis of Peptides Derived from Alpha–Methylamine", *Tetrahedron,* 11, 39–51 (1960).

*Primary Examiner*—Laura L. Stockton
*Attorney, Agent, or Firm*—Heller Ehrman White & McAuliffe

[57] ABSTRACT

A method of preparing 2-[2-{[3-(1H-benzimidazol-2-yl)propyl]methylamino)}ethyl]-6-fluoro-1-isopropyl-1,2,3,4-tetrahydronaphthalen-2-yl methoxyacetate comprises contacting 6-fluoro-1-isopropyl-3,4-dihydro-1H-naphthalen-2-one with the dianion of N-[3-(1H-benzimidazol-2-yl)propyl]-N-methylacetamide to form N-[3-(1H-benzimidazol-2-yl)propyl]-2-(6-fluoro-2-hydroxy-1-isopropyl-1,2,3,4-tetrahydronaphthalen-2-yl)-N-methylacetamide, reducing this to 2-[2-{[3-(1H-benzimidazol-2-yl)propyl]methylamino}ethyl]-6-fluoro-1-isopropyl-1,2,3,4-tetrahydronaphthalen-2-ol, and treating the 2-[2-{[3-(1H-benzimidazol-2-yl)propyl]methylamino}ethyl]-6-fluoro-1-isopropyl-1,2,3,4-tetrahydronaphthalen-2-ol with methoxyacetic acid or an activated derivative of methoxyacetic acid. The invention is particularly applicable to the preparation of mibefradil, (1S,2S)-2-[2-{[3-(1H-benzimidazol-2-yl)propyl]methylamino}ethyl]-6-fluoro-1-isopropyl-1,2,3,4-tetrahydronaphthalen-2-yl methoxyacetate, and its dihydrochloride salt. N-[3-(1H-Benzimidazol-2-yl)propyl]-N-methylacetamide, and the acetic acid solvate of 2-[2- {[3-(1H-benzimidazol-2-yl)propyl]methylamino}ethyl]-6-fluoro-1-isopropyl-1,2,3,4-tetrahydronaphthalen-2-ol dioxalate, are new.

19 Claims, No Drawings

PREPARATION OF MIBEFRADIL VIA AN ACETAMIDE ANION

CROSS-REFERENCE TO RELATED APPLICATIONS

This application claims the benefit under 35 USC 119(e) of provisional application No. 60/045,151, filed Apr. 30, 1997, which is incorporated herein by reference in its entirety.

The subject matter of this application is related to the subject matter of application Ser. No. 09/060,168 (Attorney Docket No. 22138-1005), entitled "PREPARATION OF MIBEFRADIL VIA A NAPHTHALENYLACETIC ACID", and of application Ser. No. 09/060,401 (Attorney Docket No. 22138-1006), entitled "PREPARATION OF MIBEFRADIL VIA AN ACETONITRILE ANION", both filed simultaneously with this application. Application Ser. No. 09/060,168 claims the benefit under 35 USC 119(e) of provisional application No. 09/060,168, filed Apr. 30, 1997, and application Ser. No. 09/060,401 claims the benefit under 35 USC 119(e) of provisional application No. 60/045,150, filed Apr.30, 1997. These applications and other documents referred to elsewhere in the specification of this application are incorporated herein by reference in their entirety.

BACKGROUND OF THE INVENTION

This invention relates to the preparation of mibefradil and its dihydrochloride salt.

U.S. Pat. No. 4,808,605 (to Hoffmann-La Roche) discloses various calcium antagonists including mibefradil, (1S,2S)-2-[2-{[3-(1H-benzimidazol-2-yl)propyl]-methylamino}ethyl]-6-fluoro-1-isopropyl-1,2,3,4-tetrahydronaphthalen-2-yl methoxyacetate, the dihydrochloride salt of which is the active ingredient of the antihypertensive POSICOR®. The synthesis of mibefradil, as described in that patent, involves the reaction of (1 S,2S)-6-fluoro-1-isopropyl-2-[2-(4-toluenesulfonyloxy)ethyl]-1,2,3,4-tetrahydronaphthalene-2-ol with [3-(1H-benzimidazol-2-yl)propyl]methylamine in the presence of H ünig base (ethyldiisopropylamine) to form (1S,2S)-2-[2-{[3-(1H-benzimidazol-2-yl)propyl]methylamino}ethyl]-6-fluoro-1-isopropyl-1,2,3,4-tetrahydronaphthalen-2-ol, which is then acylated with methoxyacetyl chloride in chloroform in the presence of ethyldiisopropylamine to form mibefradil.

The (1S,2S)-6-fluoro-1-isopropyl-2-[2-(4-toluenesulfonyloxy)ethyl]-1,2,3,4-tetrahydronaphthalene-2-ol, as described in U.S. Pat. No. 4,680,310 (also to Hoffmann-La Roche), is prepared by reacting (S)-6-fluoro-1-isopropyl-3,4-dihydro-1H-naphthalen-2-one with tert-butyl bromoacetate in the presence of activated magnesium to form tert-butyl (1S,2S)-(6-fluoro-2-hydroxy-1-isopropyl-1,2,3,4-tetrahydronaphthalen-2-yl)acetate, which is reduced with lithium aluminum hydride to form (1S,2S)-6-fluoro-2-(2-hydroxyethyl)-1-isopropyl-1,2,3,4-tetrahydronaphthalen-2-ol, and then reacted with 4-toluenesulfonyl chloride in pyridine to form the (1S,2S)-6-fluoro-1-isopropyl-2-[2-(4-toluenesulfonyloxy)ethyl]-1,2,3,4-tetrahydronaphthalene-2-ol.

It would be of value to have a method for the preparation of mibefradil and mibefradil dihydrochloride that affords the desired compounds easily and in reproducible high yield and purity, and is readily adaptable to large scale commercial production.

BRIEF SUMMARY OF THE INVENTION

In a first aspect, this invention provides a method of preparing N-[3 -(1H-benzimidazol-2-yl)propyl]-2-(6-fluoro-2-hydroxy-1-isopropyl-1,2,3,4-tetrahydronaphthalen-2-yl)-N-methylacetamide, and in particular its (1S,2S)-enantiomer, comprising contacting 6-fluoro-1-isopropyl-3,4-dihydro-1H-naphthalen-2-one, and in particular its (S)-enantiomer, with the dianion of N-[3-(1H-benzimidazol-2-yl)propyl]-N-methyl-acetamide.

In a second aspect, this invention provides a method of preparing 2-[2-{[3-(1H-benzimidazol-2-yl)propyl]methylamino}ethyl]-6-fluoro-1-isopropyl-1,2,3,4-tetrahydronaphthalen-2-ol, and in particular its (1S,2S)-enantiomer, comprising preparing N-[3-(1H-benzimidazol-2-yl)propyl]-2-(6-fluoro-2-hydroxy-1-isopropyl-1,2,3,4-tetrahydronaphthalen-2-yl)-N-methylacetamide, and in particular its (1S,2S)-enantiomer, as described above, and reducing the product, especially with a metal hydride.

In a third aspect, this invention provides 2-[2-{[3-(1H-benzimidazol-2-yl)propyl]-methylamino}ethyl]-6-fluoro-1-isopropyl-1,2,3,4-tetrahydronaphthalen-2-ol dioxalate as the acetic acid solvate, and in particular its (1S,2S)-enantiomer.

In a fourth aspect, this invention provides a method for preparing the 2-[2-{[3-(1H-benzimidazol-2-yl)propyl]methylamino}ethyl]-6-fluoro-1-isopropyl-1,2,3,4-tetrahydronaphthalen-2-ol dioxalate acetic acid solvate, and in particular its (1S,2S)-enantiomer, comprising contacting a solution of 2-[2-{[3-(1H-benzimidazol-2-yl)-propyl]methylamino}ethyl]-6-fluoro-1-isopropyl-1,2,3,4-tetrahydronaphthalen-2-ol in acetic acid with oxalic acid.

In a fifth aspect, this invention provides a method of preparing 2-[2-{[3-(1H-benzimidazol-2-yl)propyl]methylamino}ethyl]-6-fluoro-1-isopropyl-1,2,3,4-tetrahydronaphthalen-2-yl methoxyacetate and its acid addition salts, and in particular its (1S,2S)-enantiomer, comprising preparing 2-[2-{[3-(1H-benzimidazol-2-yl)-propyl]methylamino}ethyl]-6-fluoro-1-isopropyl-1,2,3,4-tetrahydronaphthalen-2-ol, and in particular its (1S,2S)-enantiomer, as described above, and contacting the product with methoxyacetic acid or an activated derivative of methoxyacetic acid, optionally followed by formation of an acid addition salt, especially the dihydrochloride salt.

In a sixth aspect, this invention provides N-[3-(1H-benzimidazol-2-yl)propyl]-N-methylacetamide.

In a seventh aspect, this invention provides a method of preparing N-[3-(1H-benzimidazol-2-yl)propyl]-N-methylacetamide, comprising contacting [3-(1H-benzinidazol-2-yl)propyl]methylamine with isopropenyl acetate.

In particular, this invention relates to the preparation of mibefradil, (1S,2S)-2-[2-{[3-(1H-benzimidazol-2-yl)propyl]methylamino}ethyl]-6-fluoro-1-isopropyl-1,2,3,4-tetrahydronaphthalen-2-yl methoxyacetate, and its dihydrochloride salt.

DETAILED DESCRIPTION OF THE INVENTION

While the invention will be generally described with reference to the preparation of mibefradil, it will be apparent to one of ordinary skill in the art that the reaction of (R)-6-fluoro-1-isopropyl-3,4-dihydro-1H-naphthalen-2-one with the acetamide dianion will result in the preparation of (1R,2R)- N-[3-(1H-benzimidazol-2-yl)propyl]-2-(6-fluoro-2-hydroxy-1-isopropyl-1,2,3,4-tetrahydronaphthalen-2-yl)-N-methylacetamide, which may be used to prepare the (1R,2R)-enantiomer of U.S. Pat. No. 5,120,759 in the same manner as the (1S,2S)-isomer is used here to prepare mibefradil. Accordingly, unless the context requires otherwise, reference to any compound is to be considered as a reference to individual enantiomers of the compound, and to racemic or non-racemic mixtures thereof.

The process of this invention may be represented schematically as follows:

such as ethers, e.g. tetrahydrofuran and bis(2-methoxyethyl ether), dimethylformamide, N-methylpyrrolidone, dimethylsulfoxide, etc. The solvent may also contain minor proportions of aprotic non-polar solvents such as

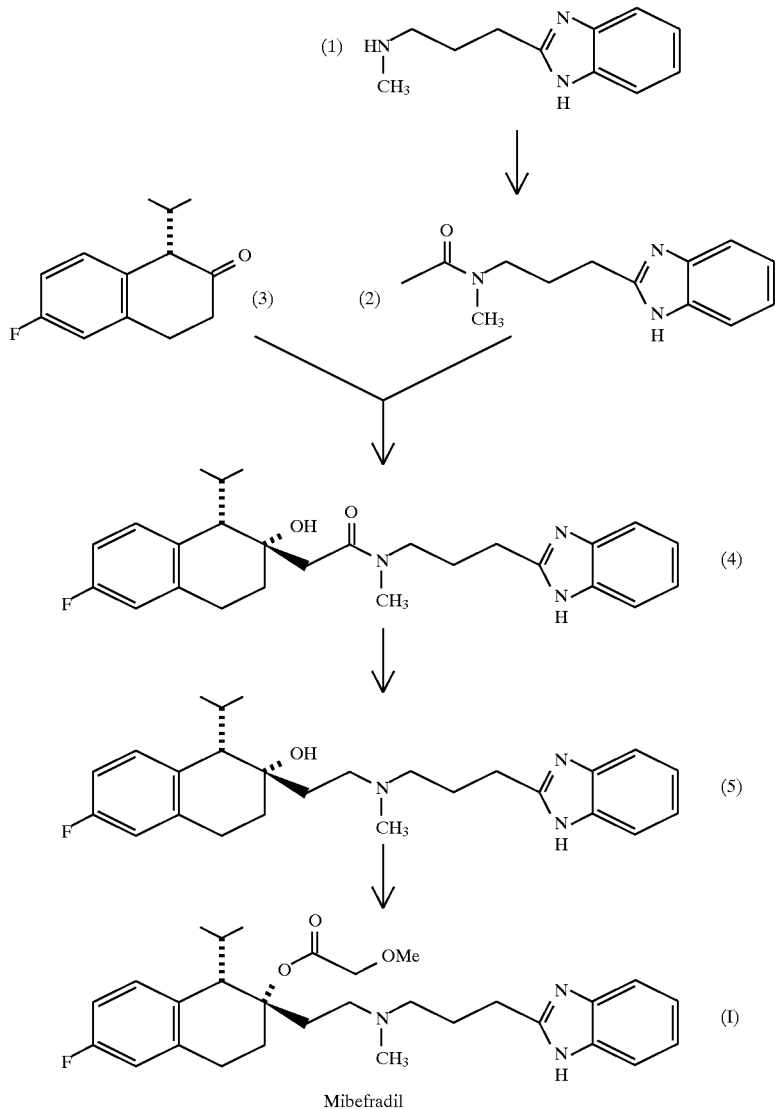

Definitions

An "activated derivative" of acetic acid is a derivative that renders the acid more active in the acylation of [3-(1H-benzimidazol-2-yl)propyl]methylamine. Typical such derivatives include acetyl halides, acetic anhydride, and certain acetate esters; and a preferred activated derivative is isopropenyl acetate.

An "activated derivative" of methoxyacetic acid is a derivative that renders the acid more active in the esterification of 2-[2-{[3-(1H-benzimidazol-2-yl)propyl]methylamino}-ethyl]-6-fluoro-1-isopropyl-1,2,3,4-tetrahydronaphthalen-2-ol. Typical such derivatives include methoxyacetyl halides and methoxyacetyl anhydride, and a preferred activated derivative is methoxyacetyl chloride.

An "aprotic polar solvent" includes organic solvents that may be either water-immiscible, such as halogenated hydrocarbons, e.g. methylene chloride, or water-miscible, hydrocarbons, e.g. cyclohexane, toluene, etc., provided that the solvent properties are largely determined by the polar solvent.

Starting Materials

Compound 1. [3-(1H-Benzimidazol-2-yl)propyl] methylamine is known, for example, from U.S. Pat. No. 4,808,605, where its preparation from 4-[1-benzyloxy-N-methylformamido]butyric acid is disclosed.

Compounds 3. 6-Fluoro-1-isopropyl-3,4-dihydro-1H-naphthalen-2-one and its (S)-isomer are known, for example, from U.S. Pat. No. 4,680,310, where their preparation from 2-(4-fluorophenyl)-3-methylbutyric acid and its (S)-isomer are disclosed. (R)-6-Fluoro-1-isopropyl-3,4-dihydro-1H-naphthalen-2-one is known, for example, from U.S. Pat. No. 5,120,759, where its preparation from (R)-2-(4-fluorophenyl)-3-methyl-butyric acid is disclosed.

All other reagents and solvents are readily commercially available, for example from Aldrich Chemical Company or equivalent suppliers.

The Process

In the first step, [3-(1H-benzimidazol-2-yl)propyl] methylamine, compound 1, is converted to N-[3-(1H-benzimidazol-2-yl)propyl]-N-methylacetamide, compound 2. This reaction may be performed by any of the methods conventional in the art for the acylation of an amine, such as by the reaction of amine (1) with acetic acid or an activated derivative of acetic acid. A preferred method is by the reaction of amine (1) with a reagent that strongly preferentially acylates only the methylamine nitrogen, such as isopropenyl acetate. The amine (1) is reacted with isopropenyl acetate, either neat (if sufficient excess isopropenyl acetate is used) or in an organic solvent such as toluene, at a sufficient temperature and for a sufficient time to cause essentially complete formation of acetamide (2) while not causing substantial formation of the diacylated product N-[3-(1-acetyl-1H-benzimidazol-2-yl)propyl]-N-methylacetamide. Acetone, the byproduct of the acylation, may be removed by distillation if desired. The resulting solution of the acetamide (2) may be used as-is in the second step of the process, or the acetamide (2) may be isolated if desired. Other activated derivatives of acetic acid may be used, but common reagents such as acetic anhydride and acetyl chloride tend to produce noticeable quantities (10% and 50% respectively) of the diacylated product on complete formation of the acetamide (2), thus requiring partial hydrolysis (such as with a strong base in a lower alkanol) to produce the acetamide (2) relatively free of the diacylated product. Acetamide (2) is new.

In the second step, the dianion of the acetamide (2) is formed, and is reacted with (S)-6-fluoro-1-isopropyl-3,4-dihydro-1H-naphthalen-2-one, compound 3, to form N-[3-(1H-benzimidazol-2-yl)propyl]-2-(6-fluoro-2-hydroxy-1-isopropyl-1,2,3,4-tetrahydronaphthalen-2-yl)-N-methylacetamide, compound 4. Typically, the acetamide (2), in solution in an aprotic polar solvent, is reacted with a strong base, such as lithium diisopropylamide (preferred) or an alkyllithium or aryllithium such as butyllithium, also in solution in an aprotic solvent, to form the acetamide dianion. The tetralone (3), typically in solution, is added gradually to the solution of the acetamide dianion. The reaction with the acetamide dianion preferably takes place at a reduced temperature, such as at −78° C.; but may take place at less extreme temperatures, such as at a temperature between about −20° C. and 8° C., if a lithium halide, such as lithium chloride (preferred) or lithium bromide, in an excess generally between two- and five-fold, is added to the acetamide dianion solution before the addition of the tetralone (3). A preferred aprotic solvent for the formation of the acetamide dianion and the subsequent reaction with tetralone (3) is tetrahydrofuran. Following completion of the addition of the tetralone (3), the reaction mixture is allowed to warm, and is then quenched with water or aqueous acid. The amide-alcohol (4) may be isolated from the reaction mixture by any suitable method: a convenient method is extraction of the amide-alcohol (4) into a water-immiscible organic solvent, such as diethyl ether and the like, followed by evaporation of the solvent; and it may be purified by recrystallization from solvents such as toluene. The amide-alcohol (4) is new.

In the third step, the amide-alcohol (4) is reduced to (1S,2S)-2-[2-{[3-(1H-benzimidazol-2-yl)propyl] methylamino}ethyl]-6-fluoro-1-isopropyl-1,2,3,4-tetrahydronaphthalen-2-ol, compound 5. The reduction is performed with a reducing agent having a high degree of specificity for the reduction of the amide carbonyl group to a methylene group without affecting other portions of the molecule; and suitable reducing agents include the metal hydrides, in particular sodium bis(2-methoxyethoxy)-aluminum hydride. Typically, the amide-alcohol (4), in solution in an organic solvent such as toluene, is treated with an excess of the reducing agent (approximately 2.25–3 equivalents when the reducing agent is sodium bis(2-methoxyethoxy)aluminum hydride), also in solution, by addition of the amide-alcohol (4) to the reducing agent, though the reverse addition is also satisfactory. The crude amide-alcohol (4) solution from the previous step may be used without purification in this step. A typical temperature for the addition is between −5° C. and 10° C.; and the reaction is then allowed to continue to completion, typically for approximately 20–24 hours at room temperature or 2–3 hours at 40°–45° C. Following completion of the reaction, the reaction mixture is quenched with aqueous base. A typical isolation procedure for the resulting alcohol (5) involves extraction into a water-immiscible organic solvent, such as the toluene used as the reaction solvent.

The alcohol (5) may be isolated if desired by conventional methods, such as by drying of the solution containing it with a drying agent such as anhydrous sodium sulfate and evaporation of the solvent. However, it will preferably be isolated as an acid addition salt, such as the dioxalate salt. Preparation and isolation of the dioxalate salt may be performed by conventional methods for the formation of acid addition salts. A presently preferred method, using acetic acid as the solvent, is shown in the Example: the use of acetic acid as solvent is valuable in that it gives the dioxalate salt of the alcohol (5) in especially pure form.

In the fourth step, the alcohol (5) is esterified with methoxyacetic acid or an activated derivative of methoxyacetic acid to form mibefradil, (1S,2S)-2-[2-{[3-(1H-benzimidazol-2-yl)propyl]methylamino}ethyl]-6-fluoro-1-isopropyl-1,2,3,4-tetrahydronaphthalen-2-yl methoxyacetate, compound I, which is typically isolated as an acid addition salt, especially the dihydrochloride salt. This esterification reaction is known from U.S. Pat. No. 4,808,605, where it is performed with methoxyacetyl chloride in chloroform in the presence of ethyldiisopropylamine; and it will be evident to one of ordinary skill in the art that methoxyacetic acid or other activated derivatives of methoxyacetic acid and other reaction conditions such as are typical in esterification of alcohols may be used. A presently preferred esterification reaction, also using methoxyacetyl chloride, but with toluene as solvent and potassium carbonate sesquihydrate as base, is shown in the Example.

Mibefradil (I) may be isolated as the free base if desired, but will preferably be isolated as an acid addition salt, more preferably as the dihydrochloride salt. The preparation and isolation of mibefradil dihydrochloride may be performed by conventional methods, such as by contacting a solution of mibefradil with a solution of hydrogen chloride in a lower alkanol, followed by crystallization of the salt, as shown in the Example.

The invention is illustrated by the following Example.

Preparation of N-[3-(1H-benzimidazol-2-yl)propyl]-N-methylacetamide.

[3-(1H-Benzimidazol-2-yl)propyl]methylamine, 5.35 g (28 mmol), was placed in a 100 mL flask, equipped with a reflux condenser and containing a magnetic stirrer bar. Toluene, 12.5 mL, was added, and the slurry stirred. Isopropenyl acetate, 12.5 mL (11.42 g, 114 mmol) was added by syringe, with continued stirring. The reaction mixture was heated to reflux temperature, and stirred at that temperature for 1.75 hours, with reaction completion monitored occasionally by thin-layer chromatography (silica gel, eluting with 70% ethyl acetate/30% methanol). The product, N-[3-(1H-benzimidazol-2-yl)propyl]-N-methylacetamide, was obtained in essentially quantitative yield in the toluene solution.

Preparation of (1S,2S)-N-[3-(1H-benzimidazol-2-yl)propyl]-2-(6-fluoro-2-hydroxy-1-isopropyl-1,2,3,4-tetrahydronaphthalen-2-yl)-N-methylacetamide.

Under a dry nitrogen atmosphere, a 2.5 molar solution of butyllithium in hexane, 8.4 mL (21 mmol) was added by syringe to 20 mL pentane. The solution was cooled to 0° C. and 2.75 mL (2.13 g, 21 mmol) diisopropylamine was added by syringe over six minutes. The solution was warmed to 25° C. and stirred for three hours, then volatiles were removed in vacuo. Tetrahydrofuran, 20 mL, was added via syringe to the residue, and the resulting yellow solution cooled to 0° C. A solution of 2.42 g (10.5 mmol) N-[3-(1H-benzimidazol-2-yl)propyl]-N-methylacetamide in 10 mL tetrahydrofuran was added by syringe over nine minutes. The yellow solution was stirred at 0° C. for fifteen minutes, then cooled to −78° C. (S)-6-Fluoro-1-isopropyl-3,4-dihydro-1H-naphthalen-2-one, 2.166 g, 87.2% pure, 97.6:2.4 S:R, in 2 mL toluene was added by syringe over twelve minutes, and a further 2 mL toluene was used to complete the transfer. After stirring at −78° C. for two hours, the viscous yellow mixture was added to 50 mL water at less than 10° C. The suspension that formed was extracted with 50 mL diethyl ether, then with a further 25 mL diethyl ether; and the combined ether extracts were dried over anhydrous magnesium sulfate, filtered, and concentrated in vacuo to afford 3.74 g of impure (1S,2S)-N-[3-(1H-benzimidazol-2-yl)propyl]-2-(6-fluoro-2-hydroxy-1-isopropyl-1,2,3,4-tetrahydronaphthalen-2-yl)-N-methylacetamide as a yellow foam. The foam was recrystallized from 6–8 mL toluene, and washed on the filter with 5 mL of toluene at −30° C. to afford 2.69 g of (1S,2S)-N-[3-(1H-benzimidazol-2-yl)propyl]-2-(6-fluoro-2-hydroxy-1-isopropyl-1,2,3,4-tetrahydronaphthalen-2-yl)-N-methylacetamide as a colorless solid, m.p. 132°–138° C. This material may be recrystallized a second time from toluene to remove residual (S)-6-fluoro-1-isopropyl-3,4-dihydro-1H-naphthalen-2-one if necessary and desired.

Lithium chloride, 22.7 g (0.54 mol) was dried at 105° C. under vacuum, then charged to a 1flask, and 100 mL tetrahydrofuran was added. The mixture was cooled to −10° C. to −15° C., and 160 mL 2 molar lithium diisopropylamide (0.32 mol) in heptane/tetrahydrofuran/ethylbenzene was added. A solution of 36.6 g (0.16 mol) N-[3-(1H-benzimidazol-2-yl)-propyl]-N-methylacetamide in 140 mL toluene was added, the solution was stirred for two hours, and a further 155 mL toluene was added. (S)-6-Fluoro-1-isopropyl-3,4-dihydro-1-H-naphthalen-2-one, 29.9 g (0.15 mol), in 15 mL toluene was added, and rinsed in with a further 5 mL toluene. After stirring at −10° to -15° C. for four hours, the resulting solution was added to 200 mL ice water. The pH of the resulting mixture was adjusted to 7–8 by addition of approximately 71 g concentrated hydrochloric acid. The organic and aqueous layers were separated, and the organic layer washed with 100 mL water, then the solvents removed under reduced pressure to give 96 g of a brown oil. Toluene, 250 mL, was added, and the mixture seeeded with about 20 mg crystalline (1S,2S)-N-[3-(1H-benzimidazol-2-yl)-propyl]-2-(6-fluoro-2-hydroxy-1 -isopropyl-1,2,3,4-tetrahydronaphthalen-2-yl)-N-methylacetamide. The mixture was heated to 65° C. to dissolve the (1S,2S)-N-[3-(1H-benzimidazol-2-yl)propyl]-2-(6-fluoro-2-hydroxy-1-isopropyl-1,2,3,4-tetrahydronaphthalen-2-yl)-N-methylacetamide, cooled to 60° C., then seeded with a further 20 mg crystalline (1S,2S)-N-[3-(1H-benzimidazol-2-yl)propyl]-2-(6-fluoro-2-hydroxy-1-isopropyl-1,2,3,4-tetrahydronaphthalen-2-yl)-N-methylacetamide. The soilution was aged at 60° C. for one hour, then cooled slowly overnight to room temperature, filtered, and the precipitate washed with 50 mL toluene at room temperature. The precipitate was dried under vacuum at 50° C. to give 45,3 g (1S,2S)-N-[3-(1H-benzimidazol-2-yl)propyl]-2-(6-fluoro-2-hydroxy-1-isopropyl-1,2,3,4-tetrahydronaphthalen-2-yl)-N-methylacetamide. Further (1S,2S)-N-[3-(1H-benzimidazol-2-yl)propyl]-2-(6-fluoro-2-hydroxy-1-isopropyl-1,2,3,4-tetrahydronaphthalen-2-yl)-N-methylacetamide could be recovered from the filtrate.

Preparation of (1S,2S)-2-[2-{[3-(1H-benzimidazol-2-yl)propyl]methylamino}ethyl]-6-fluoro-1-isopropyl-1,2,3,4-tetrahydronaphthalen-2-ol.

(1S,2S)-N-[3-(1H-Benzimidazol-2-yl)propyl]-2-(6-fluoro-2-hydroxy-1-isopropyl-1,2,3,4-tetrahydronaphthalen-2-yl)-N-methylacetamide, 20.22 g (45.7 mmol), dissolved in 200 mL toluene at 40° C., was added by cannula over 40 minutes at 0°–5° C. to a suspension of sodium bis(2-methoxyethoxy)aluminum hydride in toluene, 40 mL (41.44 g suspension, 26.94 g sodium bis(2-methoxyethoxy)aluminum hydride, 133 mmol), and a further 20 mL toluene used to complete the transfer. After completion of the addition, the mixture was stirred at 0° C. for 15 minutes, then at 35°–40° C. for three hours.

The mixture was cooled to 25° C. then added carefully to 70 g sodium hydroxide in 140 g ice at less than 10° C. Toluene, 25 mL, was used to complete the transfer. The resulting suspension was warmed to 25° C. over 30 minutes, and the phases were separated. The aqueous phase was extracted with 25 mL toluene; and the combined toluene phase was washed twice with 50 mL 10% aqueous sodium hydroxide, once with 50 mL water, then once with 50 mL saturated brine. The toluene phase was dried over magnesium sulfate, filtered, and concentrated *in vacuo* to afford 20.61 g of (1S,2S)-2-[2-{[3-(1H-benzimidazol-2-yl)propyl]methylamino}ethyl]-6-fluoro-1-isopropyl-1,2,3,4-tetrahydronaphthalen-2-ol as a colorless foam.

Preparation of (1S,2S)-2-[2-{[3-(1H-benzimidazol-2-yl)propyl]methylamino}ethyl]-6-fluoro-1-isopropyl-1,2,3,4-tetrahydronaphthalen-2-ol dioxalate.

Acetic acid, 120 mL, was added to a concentrated toluene solution (15–20 mL) containing approximately 10 g (1S,2S)-2-[2-{[3-(1H-benzimidazol-2-yl)propyl]-methylamino}ethyl]-6-fluoro-1-isopropyl-1,2,3,4-tetrahydronaphthalen-2-ol. An azeotropic mixture of acetic acid and toluene was distilled at ambient pressure until the volume was reduced to about 50 mL. Oxalic acid dihydrate, 5.44 g, was added to the solution, and the solution was stirred at approximately 100° C. for fifteen minutes. The solution was then allowed to cool slowly to 45° C., held at that temperature for two hours, allowed to cool further to 30° C., and held at that temperature for another one hour. A precipitate of (1S,2S)-2-[2-{[3-(1H-benzimidazol-2-yl)propyl]methylamino}ethyl]-6-fluoro-1-isopropyl-1,2,3,4- tetrahydronaphthalen-2-ol dioxalate formed during this cooling. The mixture was filtered at 30° C., and the warm filtrate was used to rinse residual precipitate onto the filter. The filter cake was washed three times with 10 mL acetic acid at room temperature and dried in a vacuum oven at 55°–60° C. under nitrogen flow for eighteen hours to give 9.32 g (1S,2S)-2-[2-{[3-(1H-benzimidazol-2-yl)propyl]methylamino}ethyl]-6-fluoro-1-isopropyl-1,2,3,4-tetrahydronaphthalen-2-ol dioxalate as a white solid, containing one molecule of acetic acid of crystallization per molecule of the dioxalate acid addition salt, m.p. ~130° C. with decomposition.

Preparation of mibefradil and mibefradil dihydrochloride.

To a 1 L flask was added 41.0 g (actual) (1S,2S)-2-[2-{[3-(1H-benzimidazol-2-yl)propyl]methylamino}ethyl]-6-fluoro-1-isopropyl-1,2,3,4-tetrahydronaphthalen-2-ol dioxalate, 240 mL water, and 240 mL toluene, with stirring. Potassium hydroxide pellets, 22.4 g, were added, and the mixture heated to 45°–50° C. for one hour, with continued stirring. The resulting two-phase mixture was separated using a separatory funnel while still warm. The organic phase was washed with 65 mL water and then vacuum filtered through CELATOM® (diatomaceous earth filter agent).

To the organic phase was added 39.4 g (4.0 equivalents) potassium carbonate sesquihydrate; then a solution of 21.0 g (17.7 mL, 3.25 equivalents) methoxyacetyl chloride in 33 mL toluene was added over two hours at 25°–30° C., and the resulting mixture stirred for an additional 30 minutes at that temperature. Water, 200 mL, was added at room temperature to quench the reaction; and the phases separated using a separatory funnel. The organic phase, containing mibefradil as the free base, was washed with 66 mL water. The washed organic phase was vacuum filtered through a pad of CELATOM®; and most of the toluene removed by distillation at 50° C. and 4 mmHg, leaving a solution of mibefradil in approximately 10 mL toluene. Ethanol, 17.8 mL, was added, and the mixture allowed to cool to room temperature.

To the stirred mixture was added a solution of 4.4 g of hydrogen chloride in 44.6 mL (35.0 g) ethanol at 20° C., and then a further 10.2 mL (8.0 g) ethanol. The resulting mixture was heated to 50° C.; and 1.0 mL water was added, followed by a solution of 3.4 mL water in 332 mL methyl tert-butyl ether over one hour. The mixture was stirred for ten minutes at 50° C., seeded with mibefradil dihydrochloride crystals, then stirred at 50° C. for three hours. A solution of 0.6 mL water in 65 mL methyl tert-butyl ether was added over one hour, and the mixture aged for a further 1.5 hours at 50° C. The mixture was then cooled to 15° C. over two hours and aged at 15° C. for a further hour, and the resulting slurry of mibefradil dihydrochloride was filtered on a Buchner funnel and rinsed with 95 mL dry methyl tert-butyl ether. The product was dried in a vacuum oven at 50° C. to yield mibefradil dihydrochloride as the monohydrate in 95% yield.

While this invention has been described in conjunction with specific embodiments and examples, it will be evident to one of ordinary skill in the art, having regard to this disclosure, that equivalents of the specifically disclosed materials and techniques will also be applicable to this invention; and such equivalents are intended to be included within the following claims.

What is claimed is:

1. N-[3-(1H-Benzimidazol-2-yl)propyl]-N-methylacetamide.

2. A method of preparing N-[3-(1H-benzimidazol-2-yl)propyl]-N-methylacetamide comprising contacting [3-(1H-benzimidazol-2-yl)propyl]methylamine with acetic acid or an activated derivative of acetic acid.

3. The method of claim 2 where the activated derivative of acetic acid is isopropenyl acetate.

4. A method of preparing N-[3-(1H-benzimidazol-2-yl)propyl]-2-(6-fluoro-2-hydroxy-1-isopropyl-1,2,3,4-tetrahydronaphthalen-2-yl)-N-methylacetamide comprising contacting 6-fluoro-1-isopropyl-3,4-dihydro-1H-naphthalen-2-one with the dianion of N-[3-(1H-benzimidazol-2-yl)propyl]-N-methylacetamide in an aprotic polar solvent.

5. The method of claim 4 for preparing (1S,2S)-N-[3-(1H-benzimidazol-2-yl)propyl]-2-(6-fluoro-2-hydroxy-1-isopropyl-1,2,3,4-tetrahydronaphthalen-2-yl)-N-methylacetamide comprising contacting (S)-6-fluoro-1-isopropyl-3,4-dihydro-1H-naphthalen-2-one with the dianion of N-[3-(1H-benzimidazol-2-yl)propyl]-N-methylacetamide in an aprotic polar solvent.

6. The method of claim 4 where the step of contacting is carried out at approximately −78° C.

7. The method of claim 4 where the step of contacting is carried out at a temperature between about −20° C. and 8° C. in the presence of an excess of a lithium halide.

8. The method of claim 4 where the dianion of N-[3-(1H-benzimidazol-2-yl)propyl]-N-methylacetamnide is prepared by contacting N-[3-(1H-benzimidazol-2-yl)propyl]-N-methyl-acetamide with a strong base in an aprotic polar solvent.

9. The method of claim 4 further including the step of treating the thus-formed N-[3-(1H-benzimidazol-2-yl)propyl]-2-(6-fluoro-2-hydroxy-1-isopropyl-1,2,3,4-tetrahydronaphthalen-2-yl)-N-methylacetamide with a reducing agent to form 2-[2-{[3-(1H-benzimidazol-2-yl)propyl]methylamino}ethyl]-6-fluoro-1-isopropyl-1,2,3,4-tetrahydronaphthalen-2-ol.

10. The method of claim 5 further including the step of treating the thus-formed (1S,2S)-N-[3-(1H-benzimidazol-2-yl)propyl]-2-(6-fluoro-2-hydroxy-1-isopropyl-1,2,3,4-tetrahydronaphthalen-2-yl)-N-methylacetamide with a reducing agent to form (1S,2S)-2-[2-{[3-(1H-benzimidazol-2-yl)propyl]methylamino}ethyl]-6-fluoro-1-isopropyl-1,2,3,4-tetrahydronaphthalen-2-ol.

11. The method of claim 9 where the reducing agent is a metal hydride.

12. The method of claim 11 where the reducing agent is sodium bis(2-methoxyethoxy)-aluminum hydride.

13. The method of claim 9 further including the step of contacting the thus-formed 2-[2-{[3-(1H-benzimidazol-2-yl)propyl]methylamino}ethyl]-6-fluoro-1-isopropyl-1,2,3,4-tetrahydronaphthalen-2-ol with methoxyacetic acid or an activated derivative of methoxyacetic acid to form 2-[2-{[3-(1H-benzimidazol-2-yl)propyl]methylamino}ethyl]-6-fluoro-1-isopropyl-1,2,3,4-tetrahydronaphthalen-2-yl methoxyacetate.

14. The method of claim 10 further including the step of contacting the thus-formed (1S,2S)-2-[2-{[3-(1H-benzimidazol-2-yl)propyl]methylamino}ethyl]-6-fluoro-1-isopropyl-1,2,3,4-tetrahydronaphthalen-2-ol with methoxyacetic acid or an activated derivative of methoxyacetic acid to form (1S,2S)-2-[2-{[3-(1H-benzimidazol-2-yl)propyl]methylamino}ethyl]-6-fluoro-1-isopropyl-1,2,3,4-tetrahydronaphthalen-2-yl methoxyacetate.

15. The method of claim 13 where the methoxyacetic acid or an activated derivative of methoxyacetic acid is methoxyacetyl chloride, and the step of contacting occurs in the presence of a base in an aprotic solvent.

16. The method of claim 13 further including the step of forming an acid addition salt of the 2-[2-{[3-(1H-benzimidazol-2-yl)propyl]methylamino}ethyl]-6-fluoro-1-isopropyl-1,2,3,4-tetrahydronaphthalen-2-yl methoxyacetate.

17. The method of claim 16 where the acid addition salt is the dihydrochloride salt.

18. The method of claim 17 where the step of forming the dihydrochloride salt comprises reacting the 2-[2-{[3-(1H-benzimidazol-2-yl)propyl]methylamino}ethyl]-6-fluoro-1-isopropyl-1,2,3,4-tetrahydronaphthalen-2-yl methoxyacetate with a solution of hydrogen chloride in a lower alkanol.

19. The method of claim 18 where the lower alkanol is ethanol.

* * * * *